United States Patent

Chantot et al.

Patent Number: 5,378,697
Date of Patent: Jan. 3, 1995

[54] CEPHALOSPORINS

[75] Inventors: Jean-Francois Chantot, Gressy en France; Solange Gouin D'Ambrieres, Paris; Daniel Humbert, Fontenay Sous Bois; Jean-Georges Teutsch, Pantin, all of France

[73] Assignee: Roussel-UCLAF, France

[21] Appl. No.: 903,610

[22] Filed: Jun. 24, 1992

[30] Foreign Application Priority Data

Jun. 25, 1991 [FR] France .................. 91 07785

[51] Int. Cl.⁶ .................. C07D 513/04; A61K 31/54
[52] U.S. Cl. .................. 514/210; 540/214; 540/215
[58] Field of Search .............. 540/222, 225, 221, 214, 540/215; 514/210

[56] References Cited

U.S. PATENT DOCUMENTS

| | | | |
|---|---|---|---|
| 5,001,121 | 3/1991 | Ohnishi et al. | 540/227 |
| 5,075,298 | 12/1991 | Aszodi et al. | 540/225 |
| 5,262,411 | 11/1993 | Shirasaka et al. | 540/214 |

FOREIGN PATENT DOCUMENTS

| | | |
|---|---|---|
| 0405217 | 1/1991 | European Pat. Off. |
| 0520880 | 12/1992 | European Pat. Off. |

*Primary Examiner*—Nicholas Rizzo
*Attorney, Agent, or Firm*—Bierman and Muserlian

[57] ABSTRACT

The syn isomer of a compound of the formula

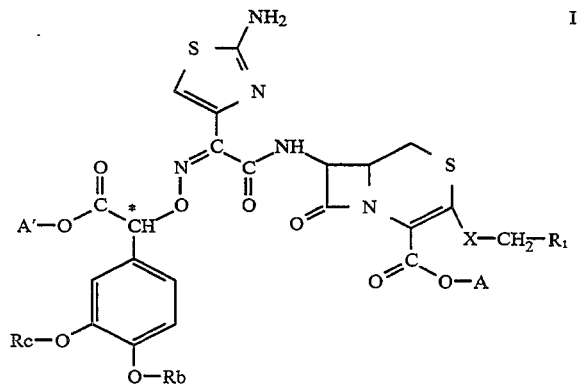

in the R or S form or a mixture of R and S forms and their non-toxic, pharmaceutically acceptable acid addition salts wherein the substituents are defined as in the specification having antibacterial activity and their preparation.

11 Claims, No Drawings

CEPHALOSPORINS

OBJECTS OF THE INVENTION

It is an object of the invention to provide the novel compounds of formula and their non-toxic, pharmaceutically acceptable salts and a novel process and novel intermediates for their preparation.

It is another object of the invention to provide novel antibacterial compositions and a novel method of combatting bacterial infections in warm-blooded animals.

These and other objects and advantages of the invention will become obvious from the following detailed description.

THE INVENTION

The novel compounds of the invention comprise the syn isomers of compounds of the formula

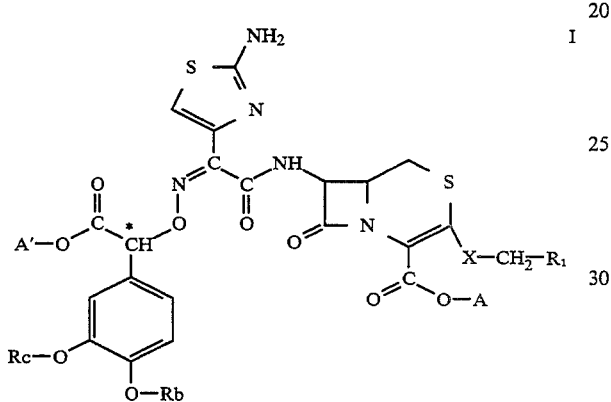

in the R or S form or a mixture of R and S forms wherein $R_1$ is selected from the group consisting of

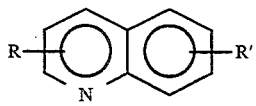

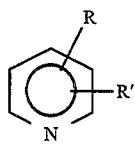

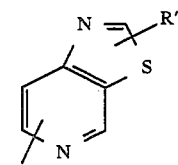

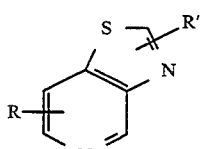

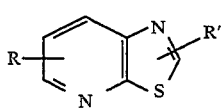

-continued

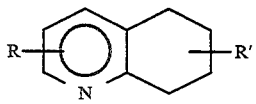

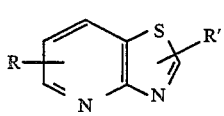

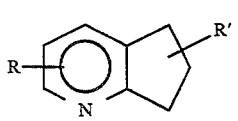

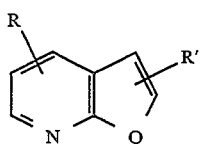

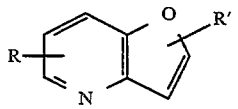

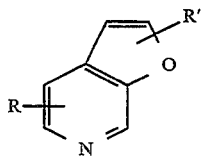

-continued
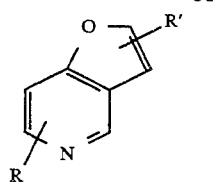
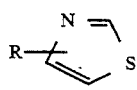
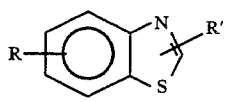
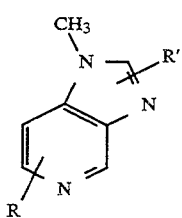
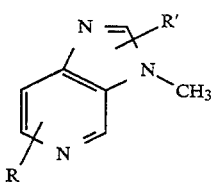
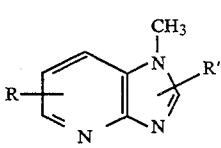
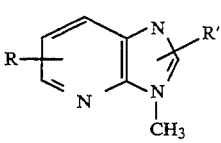
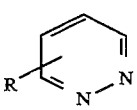
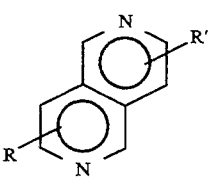
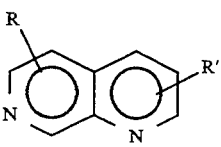
-continued
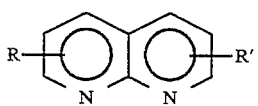
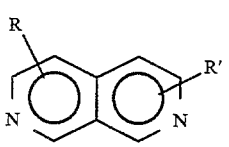
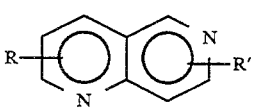
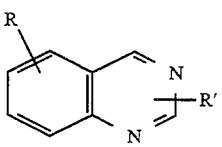
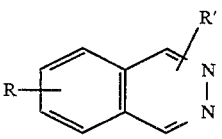
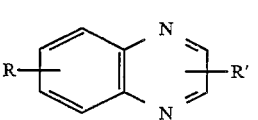
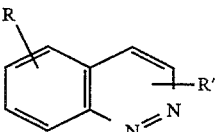
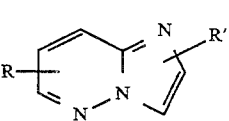
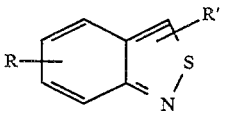
and
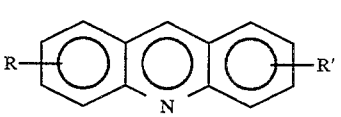
in the form of quaternary ammonium, or

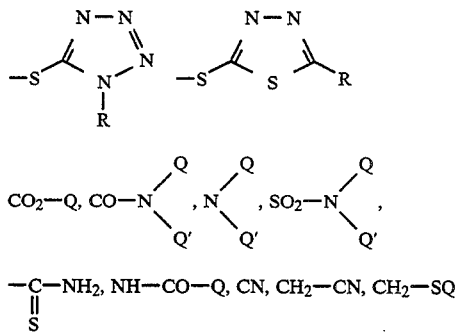

R and R' are individually selected from the group consisting of hydrogen, alkyl of 1 to 4 carbon atoms, alkoxy of 1 to 4 carbon atoms and halogen, Q and Q' are individually selected from the group consisting of hydrogen and alkyl of 1 to 4 carbon atoms, P, P' and P'' are individually alkyl of 1 to 4 carbon atoms optionally substituted by one of the substituents of R and R', the dotted line indicating that P and P' can optionally form with the nitrogen atom to which they are attached a heterocycle with 5 or 6 ring members, or $R_1$ is —S—Het wherein Het is selected from the group consisting of thiazolyl, isothiazolyl, oxazolyl, isoxazolyl, triazolyl, thiadiazolyl, oxadiazolyl, tetrazolyl, imidazolyl, pyrazolyl, pyridinyl, pyrimidinyl, pyrazinyl, pyridazinyl, triazinyl and dihydrotriazinyl, all optionally substituted by at least one substituent selected from the group consisting of alkyl of 1 to 4 carbon atoms, alkyl or dialkylamino, hydroxy, oxo, alkylthio, free, esterified or salified carboxy and carboxyalkyl, X is a single bond or $$\diagdown_{C=C}\diagup$$

in E or Z form, $R_b$ and $R_c$ are individually hydrogen or acyl, A and A' are individually selected from the group consisting of an equivalent of alkali metal or alkaline-earth metal, magnesium, ammonium and amino or A and A' are the remainder of an easily cleavable ester group or —$CO_2A$ is $CO_2$ and their non-toxic, pharmaceutically acid addition salts.

When $R_b$ and/or $R_c$ is acyl, examples are acetyl, propionyl, benzoyl or formyl. The preferred acyl is acetyl and the preferred value for $R_b$ and $R_c$ is hydrogen.

Examples of A and A' are equivalents of sodium, potassium, lithium, calcium, magnesium or ammonium or organic bases such as methylamine, propylamine, trimethylamine, diethylamine, triethylamine, N,N-dimethylethanolamine, tris (hydroxymethyl) amino methane, ethanolamine, pyridine, picoline, dicyclohexylamine, morpholine, benzylamine, procaine, lysine, arginine, histidine and N-methylglucamine.

Among others are remainders of easily cleavable ester groups that can be represented by A and A' such as methoxymethyl, ethoxymethyl, isopropyloxymethyl, alpha-methoxy ethyl, alpha-ethoxy ethyl, methylthiomethyl, ethylthiomethyl, isopropylthiomethyl, pivaloyloxymethyl, acetoxymethyl, propionyloxymethyl, butyryloxymethyl, isobutyryloxymethyl, valeryloxymethyl, isovaleryloxymethyl, tert-butylcarbonyloxymethyl, hexadecanoyloxymethyl, propionyloxyethyl, isovaleryloxyethyl, 1-acetyloxyethyl, 1-propionyloxyethyl, 1-butyryloxyethyl, 1-tert-butylcarbonyloxyethyl, 1-acetyloxypropyl, 1-hexadecanoyloxyethyl, 1-propionyloxypropyl, 1-methoxycarbonyloxyethyl, methoxycarbonyloxymethyl, 1-acetyloxybutyl, 1-acetyloxthexyl, 1-acetyloxyheptyl, phthalidyl, 5,6-dimethoxyphthalidyl, tert-butylcarbonylmethyl, allyl, 2-chloroallyl, methoxycarbonylmethyl, benzyl, tert-butyl, trityl, benzhydryl or para-methoxybenzyl.

Other examples of remainders of ester groups represented by A and A' are methoxyethoxymethyl, dimethylaminoethyl, cyanomethyl, tert-butoxycarbonylmethyl, 2,2-ethylenedioxyethyl, cyanoethyl, 2,2-dimethoxyethyl, 2-chloroethoxymethyl, 2-hydroxyethoxyethyl, 2,3-epoxypropyl, 3-dimethylamino, 2-hydroxypropyl, 2-hydroxyethyl, 2-methylaminoethoxymethyl, 2-aminoethoxymethyl, 3-methoxy-2,4-thiadiazol-5-yl, 2-tetrahydropyrannyl, 1-methoxy-1-methyl-ethyl, 2-hydroxy-1-methyl ethyl, isopropyl, carbamoylmethyl, chloromethyl, 2-chloroethyl, acetylmethyl, 2-methylthioethyl or thiocyanatomethyl as well as 2-chloro-1-acetyloxyethyl, 2-bromo-1-acetyloxyethyl, 2-fluoro-1-acetyloxypropyl, 2-methoxy-1-acetyloxyethyl, 2-methyl-1-acetyloxypropyl, 1-methyl-1-acetyloxyethyl, 1-methoxyacetyloxyethyl, 1-acetylcarbonyloxyethyl, 1-hydroxyacetyloxyethyl, 1-formylcarbonyloxyethyl, 1-(2-thienyl)-carbonyloxyethyl, 1-(2-furyl) carbonyloxyethyl, 1-(5-nitro-2-furyl)carbonyloxyethyl, 1-(2-pyrrolyl) carbonyloxyethyl, 1-(propionyloxycarbonyloxy) ethyl, 1-(propyloxycarbonyloxy) ethyl, 1-(isopropyloxycarbonyloxy) ethyl, 1-(methoxyethoxycarbonyloxy) ethyl, 1-(allyloxycarbonyloxy) ethyl, isopropyloxycarbonyl methyl, 1-[(2,3-epoxy propyl)-oxycarbonyloxy]-ethyl, 1-[(2-furyl) methyloxycarbonyloxy]ethyl, 1-(2-fluoroethyl) oxycarbonyloxyethyl, 1-(methoxycarbonyloxy)-propyl, 1-(methoxycarbonyloxy)-1-methyl ethyl, 1-(methoxycarbonyloxy)-2-chloromethyl, 1-(methoxycarbonyloxy) 2-chloroethyl, 1-(methoxycarbonyloxy) 2-methoxy ethyl, 1-(methoxycarbonyloxy) allyl, or

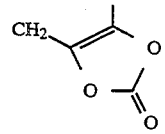

Examples of alkyl of 1 to 4 carbon atoms are methyl, ethyl, propyl, butyl, isobutyl, sec-butyl and tert-butyl and methyl is preferred. Examples of alkoxy of 1 to 4 carbon atoms are methoxy, ethoxy, propyloxy, butyloxy and methoxy is preferred.

Examples of halogen are fluorine, chlorine, bromine and iodine with fluorine, chlorine or bromine being preferred.

Heterocycles of 5 or 6 ring members that P and P' can form with the nitrogen atom to which they are linked may be piperidine, morpholine, pyrrolidine. Among the alkylamino that can be carried by the heteocycles are methylamino, ethylamino, isopropylamino and (linear or branched) butyl amino with the alkyl being 1 to 4 carbon atoms.

It is the same for the alkyl that can be carried out by the dialkylamino. Among the dialkylamino there can be mentioned for example dimethylamino, diethylamino, methylethylamino. Among the alkylthio preferred are those wherein alkyl was 1 to 4 carbon atoms such as methyl, ethyl, propyl, butyl or branched butyl with methylthio being preferred.

The carboxyalkyl can be formed with the same alkyl as those indicated above with carboxymethyl being preferred. The carboxy and carboxyalkyl can be esterified or salified as indicated above.

Among the heterocyclics represented by Het are 1,3,4, 1,2,4 or 1,2,3 thiadiazolyl; thiazol-2-yl, imidazol-2-yl; 2-methyl-1,3,4-thiadiazol-5-yl; 1-methyl tetrazol-5-yl; dihydrotriazinyls of the formulae:

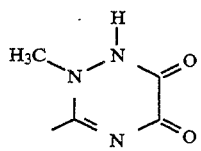

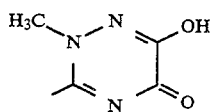

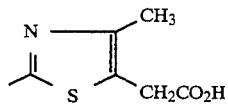

The isocephem nucleu can be in racemic or optically active form with the products in which the nucleus is (S) cis being preferred, that is (S); (S).

The products of formula I can also be presented in the form of organic or mineral acid salts. Among the acids with which the amino group or groups of the products I can be salified are acetic acid, trifluoroacetic acid, maleic acid, tartaric acid, methanesulfonic acid, benzenesulfonic acid, p-toluene sulfonic acid, phosphoric acid, sulfuric acid, hydrochloric acid, hydrobromic acid, hydroiodic acid. The products can also be presented in the form of internal salts.

In a preferred embodiment of the invention, A' is hydrogen or sodium, preferably hydrogen and $CO_2A$ is $CO_2$.

In a preferred embodiment of the invention, $R_1$ in the compounds of formula I is chosen either from:

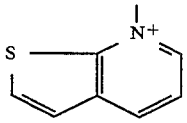

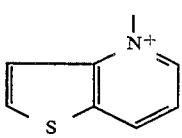

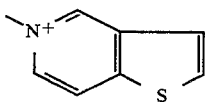

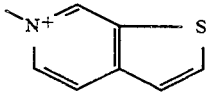

-continued

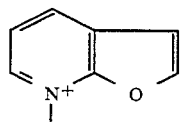

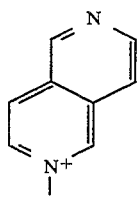

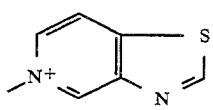

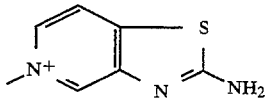

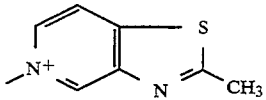

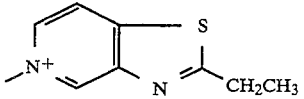

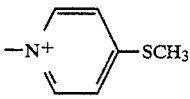

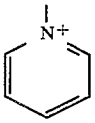

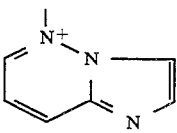

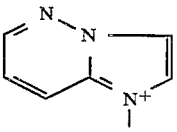

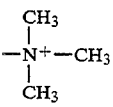

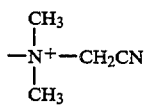
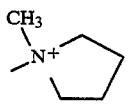
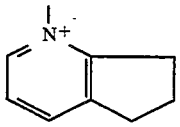
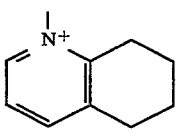
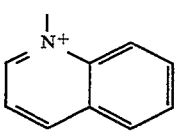
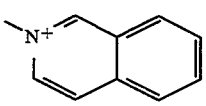
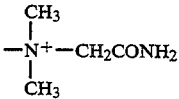
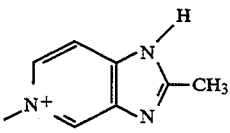
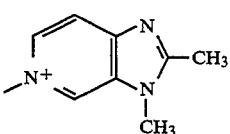
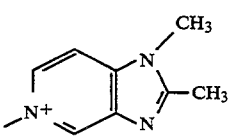
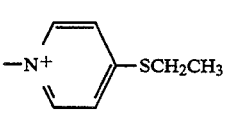
or from S-Het in which Het is selected from the group consisting of 1,2,4, 1,3,4 or 1,2,3-thiadiazolyl; thiazol-2-yl; imidazol-2-yl; 2-methyl-1,3,4-thiadiazol-5-yl; 1-methyl tetrazol-5-yl.
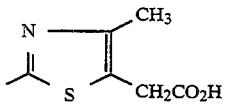
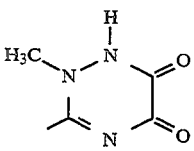
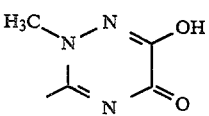
A more preferred group of compounds of formula I are those wherein $R_1$ is chosen from either
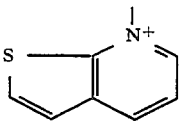
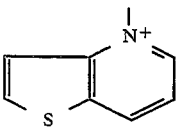
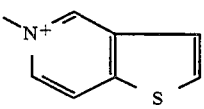
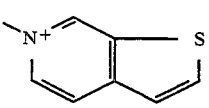
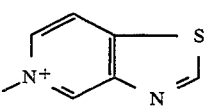
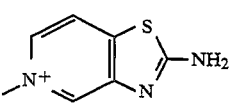
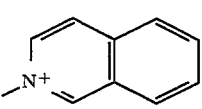
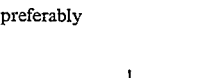
preferably
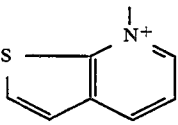
or $R_1$ is 1,3,4-thiadiazolylthio or methyltetrazolylthio.

A particular preferred compound of the invention is (S) (cis) (Z) 5-[[7-[[(2-amino-4-thiazolyl)-[carboxy-(3,4-dihydroxy phenyl)-methoxy]-imino]-acetamido]-2-carboxy-8-oxo-4-thia-1-azabicyclo-[4,2,0]-oct-2-en-3-yl]-methyl]-thieno-[2,3-b]-pyridinium in R or S form or an R,S mixture, and in the form of an internal salt or a salt with alkali metals, alkaline-earth metals, magnesium, ammonium hydroxide, amino organic bases, acids and its easily cleavable esters.

It is understood that the products of formula I can exist: either in the form of formula I or in the form of products of the formula

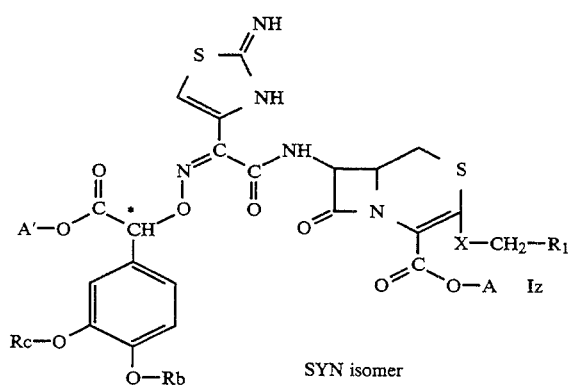

SYN isomer in which A, A', X, $R_b$, $R_c$ and $R_1$ have the above meanings

The novel process of the invention for the preparation of the compounds of formula I comprises either reacting a compound of the formula

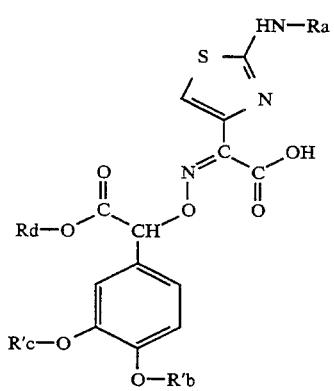

II syn, racemic or optically active isomer or a functional derivative thereof wherein $R_s$ is hydrogen or a protective group of the amino, $R'_b$ and $R'_c$ are individually hydrogen or a protective group of hydroxyl, $R_d$ is hydrogen or the remainder of an ester group which can be easily eliminated with a product of the formula

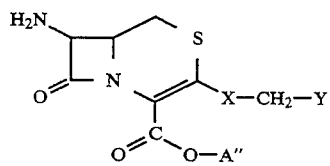

III wherein Y is hydroxy or halogen, A" is hydrogen or the remainder of an ester group which can be easily eliminated to obtain a product of the formula

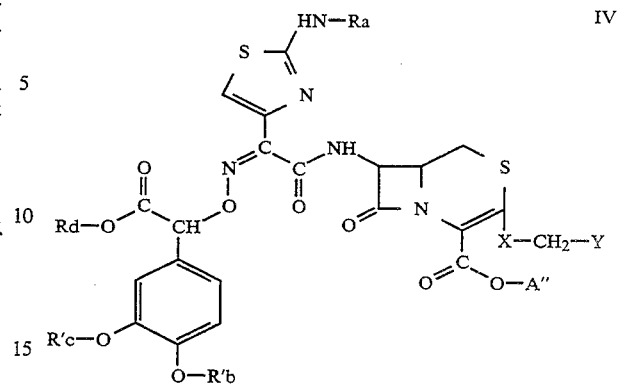

IV reacting the latter with a reagent to introduce $R_1$ to obtain a product of the formula

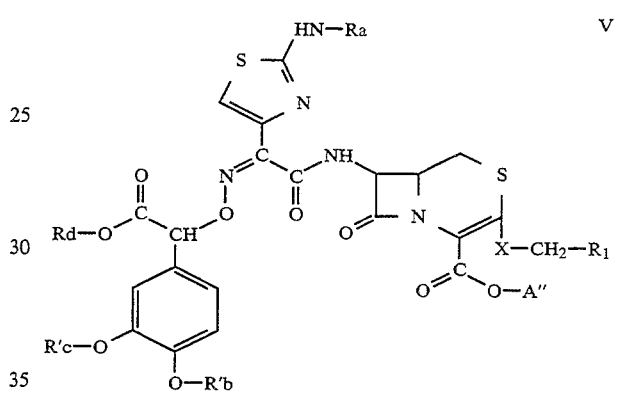

V or a product of the formula

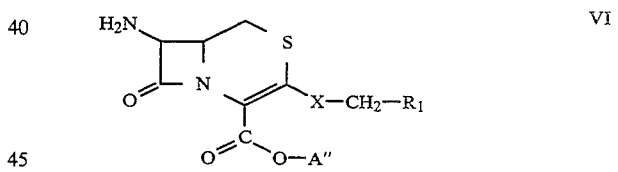

VI in which X, $R_1$ and A" have the above meanings, reacting the latter with a product of formula II as defined above or a functional derivative thereof to obtain a product of formula V as defined above, which is optionally when X is

separated into its E or Z isomers or the Z isomers are converted into E isomers and which products of formula V are, if necessary or if desired, subjected to one or more of the following reactions in any order:

a) cutting by hydrolysis or by the action of thiourea of all or part of the ester groups or the protection groups of the amino or hydroxyl, b) esterification or salification of the carboxylic(s) by a base, c) salification of the amino by an acid, d) separation of the products in the form of an R,S mixture into R or S.

In addition to the above-mentioned groups, the ester groups which are easily eliminated of A" or R$_d$ can be the ester formed with butyl, isobutyl, tert-butyl, pentyl, hexyl, acetoxymethyl, propionyloxymethyl, butyryloxymethyl, valeryloxymethyl, pivaloyloxymethyl, 2-acetoxyethyl, 2-propionyloxyethyl or 2-butyryloxyethyl or 2-iodoethyl, 2,2,2-trichloroethyl, vinyl, allyl, ethynyl, propynyl, benzyl, 4-methoxybenzyl, 4-nitrobenzyl, phenethyl, trityl, diphenylmethyl and 3,4-dimethoxyphenyl. Phenyl, 4-chloro phenyl, tolyl and tert-butylphenyl can also be mentioned with diphenylmethyl being preferred for A" and R$_d$.

The protective group of the amino represented by R$_a$ may be alkyl of 1 to 6 carbon atoms such as preferably, tert-butyl or tert-amyl. R$_a$ can also be acyl, aliphatic, aromatic or heterocyclic or carbamoyl. The lower alkanoyl such as formyl, acetyl, propionyl, butyryl, isobutyryl, valeryl, isovaleryl, oxalyl, succinyl, and pivaloyl can be mentioned.

R$_a$ may also be lower alkoxy or cycloalkoxycarbonyl such as methoxycarbonyl, ethoxycarbonyl, propoxycarbonyl, 1-cyclopropylethoxycarbonyl, isopropyloxycarbonyl, butyloxycarbonyl, tert-butyloxycarbonyl, pentyloxycarbonyl, hexyloxycarbonyl, or one of the following groups: benzoyl, toluolyl, naphthoyl, phthaloyl, methyl, phenylacetyl, phenylpropionyl or an aralkoxycarbonyl such as benzyloxycarbonyl.

The acyls can be substituted for example by chlorines bromine, iodine or fluorine such as chloroacetyl, dichloroacetyl, trichloroacetyl, bromoacetyl or trifluoroacetyl.

R$_a$ may also be lower aralkyl such as benzyl, 4-methoxybenzyl, phenethyl, trityl, 3,4-dimethoxybenzyl or benzhydryl. R$_8$ may also be haloalkyl such as trichloroethyl or chlorobenzoyl, para-nitrobenzoyl, para-tert-butylbenzoyl, phenoxyacetyl, caprylyl, n-decanoyl, acryloxy or trichloroethoxycarbonyl. R$_a$ may also be methylcarbamoyl, phenylcarbamoyl, naphthylcarbamoyl as well as the corresponding thiocarbamoyls. Trityl is preferred. The above list is not limitative and it is obvious that other amine protective groups known particularly in the chemistry of the peptides, can also be used.

The protective groups of hydroxyl that can be represented by R'$_b$ and R'$_c$ can be chosen acyl such as formyl, acetyl, propionyl, chloroacetyl, bromo-acetyl, dichloro-acetyl, trichloroacetyl, trifluoroacetyl, methoxyacetyl, phenoxyacetyl, benzoyl, benzoylformyl, p-nitrobenzoyl or ethoxycarbonyl, methoxycarbonyl, propoxycarbonyl, 2,2,2-trichloro-ethoxycarbonyl, benzyloxycarbonyl, tertbutoxycarbonyl, 1-cyclopropylethoxycarbonyl, tetrahydropyrannyl, tetrahydrothiopyrannyl, methoxytetrahydropyrannyl, trityl, benzyl, 4-methoxybenzyl, benzhydryl, trichloroethyl, 1-ethyl 1-methoxyethyl, phthaloyl. Other acyls include butyryl, isobutyryl, valeryl, isovaleryl, oxalyl, succinyl and pivaloyl or phenylacetyl, phenylpropionyl, mesyl, chlorobenzoyl, para-nitrobenzoyl, paratert-butylbenzoyl, caprylyl, acryloyl, methylcarbamoyl, phenylcarbamoyl, naphthylcarbamoyl. Alkoxymethyl can also be mentioned such as methoxyethoxymethyl.

OR'$_b$ and OR'$_c$ can also form with the phenyl to which they are attached:

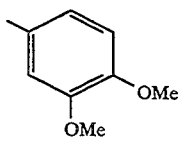

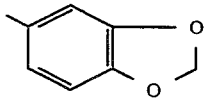

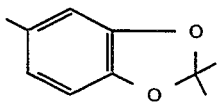

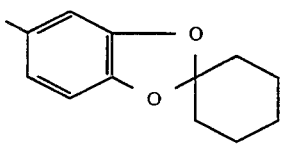

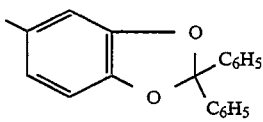

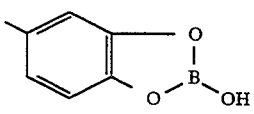

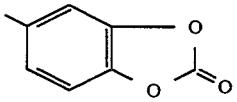

The methoxyethoxymethyl group is preferred for R'$_b$ and R'$_c$.

In a preferred embodiment of the process, a functional derivative of the product of formula II is reacted which may be for example a halide, a symmetrical or mixed anhydride, amide, azide or an activated ester. An example of a mixed anhydride is that formed with isobutyl chloroformate and that formed with pivaloyl chloride and the carboxylic-sulfonic mixed anhydrides formed for example with p-toluene sulfonyl chloride.

An example of the activated ester is the ester formed with 2,4-dinitrophenol and that formed with hydroxybenzothiazole. An example of the halide is chloride or the bromide.

The anhydride can be formed in situ by the action of N,N-disubstituted carbodiimide, for example N,N-dicyclohexylcarbodiimide, diisopropylcarbodiimide or ethyldimethylamino propyl carbodiimide. The acylation reaction is carried out preferably in an organic solvent such as methylene chloride but other solvents such as tetrahydrofuran, chloroform, acetone, water or dimethylformamide can be used.

When an acid halide is used and generally when a molecule of hydrohalic acid is released during the reaction, the reaction is preferably carried out in the presence of a base such as sodium hydroxide, potassium hydroxide, alkali metal carbonates and bicarbonates of sodium or potassium, sodium acetate, triethylamine, pyridine, morpholine or N-methylmorphotine. The reaction temperature is generally less than or equal to ambient temperature.

The product of formula II can also be directly reacted with a product of formula III in the presence of a carbodiimide such as diisopropylcarbodiimide. An example of such a preparation is given further on in the experimental part.

The reagent to introduce $R_1$ is either one of the above-indicated which are then presented, after introduction, in the form of a quaternary ammonium, or a reagent of formula Het—SH in which Het has the definition indicated above. The addition of these reagents to the product of formula IV is carried out under the following conditions:

When Y is chlorine, a substitution of the chlorine by iodine can be carried out in situ or separately, in the presence of sodium iodide and then the desired reagent is added. An example of such a reaction is described hereafter in the experimental part. The desired reagent can also be reacted on the product of formula IV when Y is chlorine in the presence of silver tetrafluoroborate.

When Y is hydroxy, the product is also converted into a product in which Y is iodine for example by the action of tetrabutyl ammonium iodide in the presence of 2,6-lutidine and methylsulfonic anhydride.

One of the reagents indicated above can also be reacted with a product of formula IV in which the hydroxy has been converted into a reactive group for example using a sulfonic anhydride such as methylsulfonic, p-toluene sulfonic or preferably trifluoromethane sulfonic anhydride.

The action of the products of Het-SH is carried out under similar conditions to those indicated above. In particular, the products of formula IV in which Y is hydroxy can be converted into a reactive derivative using a sulfonic acid derivative such as trifluoromethane sulfonic acid anhydride. The operation is preferably carried out in the presence of a base such as 2,6-lutidine, 2,4,6-collidine, tetramethylguanidine, diazabicyclononene or diazabicyclo undecene in the presence of alkylizing agent for example trifluromethylsulfonic anhydride.

The action of the products of formula II on the products of formula VI is carried out under the same conditions as for the action of the products of formula II with the products of formula III.

The isomerism of the products of formula V can be different from that of the products of formula IV used at the start. In the case where the Z isomer is isolated, this isomer can be converted into an E isomer by known methods, notably by the action of iodine.

Depending on the values of $R_a$, $R'_b$, $R'_c$, $R_d$ and A", the products of formula V can or cannot be a product of formula I. The products of formula V constitute the products of formula I when $R_a$ is hydrogen, when $R'_b$ and $R'_c$ are not a protective group of the hydroxyl which it is desired to eliminate, that is to say when $R'_b$ and/or $R'_c$ are acyl and when $R_d$ and A" are not, among the easily cleavable ester groups, one of those which it is desired to eliminate.

In the other cases, the purpose of the action on the product of formula V of one or more hydrolysis or hydrogenolysis agents or of thiourea is to eliminate the $R_a$ when the latter is a protective of the amino to eliminate $R'_b$ and $R_c$ when the latter is protective group of hydroxyl and/or to eliminate $R_d$ and A" when the latter are among the easily cleavable ester groups, one of those which it is desired to eliminate.

However, it is of course possible to eliminate $R_a$, $R'_b$ and $R'_c$ without affecting the $R_d$ and A" substituents when these have to be preserved. This is the case when A" is an ester group which it is desired to preserve such as propionyloxymethyl.

The nature of the reagents to use in such a case is well known to a man skilled in the art. Examples of such reactions are given further on in the experimental part. A description of the different elimination methods of the different protective groups will be found for example in French Patent Application No. 2,499,995.

Among the preferred protective groups are trityl for $R_a$, methoxyethoxymethyl for $R'_b$ and $R'_c$ and diphenylmethyl for $R_d$ and A". Trifluoroacetic acid is preferably used without a solvent or in a solvent such as anisole or a mixture of solvents such as anisole/methylene chloride. In that case, a salt is obtained with trifluoroacetic acid and the free base can then be returned to by the action of a base such as triethylamine carbonate. The salification of the products can be carried out according to the usual methods. The salification can be obtained by the action on a product in acid form or on a solvate, for example, ethanolic solvate or a hydrate of this acid, of a mineral base such as sodium or potassium hydroxide, sodium or potassium carbonate or bicarbonate. The salts of mineral acids such as trisodium phosphate can also be used, as well as salts of organic acids.

Examples of organic acid salts are sodium salts of saturated or unsaturated, linear or branched, aliphatic carboxylic acids of 1 to 18 and preferably 2 to 10 carbon atoms. The aliphatic chains of these acids can be interrupted by one or more heteroatoms such as oxygen or sulfur or substituted by aryl such as phenyl, thienyl, furyl, by at least one hydroxyl or halogen such as fluorine, chlorine or bromine, preferably chlorine, by carboxylic or lower alkoxycarbonyl, preferably methoxycarbonyl, ethoxycarbonyl, or propyloxycarbonyl or by aryloxy, preferably phenoxy.

Furthermore, sufficiently soluble aromatic acids can be used as organic acids, for example benzoic acids substituted preferably by lower alkyl. Examples of such organic acids are formic acid, acetic acid, acrylic acid, butyric acid, adipic acid, isobutyric acid, n-caproic acid, isocaproic acid, chloropropionic acid, crotonic acid, phenylacetic acid, 2-thienylacetic acid, 3-thienylacetic acid, 4-ethylphenylacetic acid, glutaric acid, the monoethyl ester of adipic acid, hexanoic acid, heptanoic acid, decanoic acid, oleic acid, stearic acid, palmitic acid, 3-hydroxy propionic acid, 3-methoxy propionic acid, 3-methylthio butyric acid, 4-chloro butyric acid, 4-phenylbutyric acid, 3-phenoxy butyric acid, 4-ethyl benzoic acid, 1-propyl benzoic acid. However, sodium acetate, sodium 2-ethyl hexanoate or sodium diethyl acetate are preferably used as sodium salts.

The salification can also be obtained by the action of an organic base such as triethylamine, diethylamine, trimethylamine, propylamine, N,N-dimethyl ethanolamine, tris (hydroxymethyl) amino methane, methylamine, ethanolamine, pyridine, picoline, dicyclohexyl amine, morpholine and benzylamine or by the action of arginine, lysine, procaine, histidine or N-methyl glucamine. This salification is carried out preferably in a solvent or a mixture of solvents such as water, ethyl ether, methanol, ethanol or acetone.

The salts are obtained in amorphous or crystallized form according to the reaction conditions used. The crystallized salts are prepared preferably by reacting the free acids with one of the aliphatic carboxylic acid salts mentioned above, preferably, with sodium acetate. The salification of the products by mineral or organic acids is carried out under the usual conditions.

The optional esterification of the products is carried out under standard conditions and is generally carried out by reacting the acid of formula I or a functional derivative with a derivative of the formula Z—Re in which Z is hydroxyl or halogen such as chlorine, bromine, iodine and Re is the ester group to be introduced, a non-exhaustive list of which group is set out above. In some cases, it is advantageous to carry out an esterification on a product whose amine and/or reaction groups present on the oxyimino are blocked before removing the protective group of the amine and of the reaction group present on the oxyimino.

The products of formula I contain several asymmetrical carbons. In the cephem nucleus, which contains two asymmetrical carbons, the two carbons are preferably in S configuration. Furthermore, the group present on the oxyimino function also contains an asymmetrical carbon:

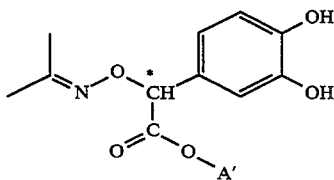

which can be in R or S form or in the form of an R,S mixture. The separation of the two diastereoisomers can be carried out by means known to one skilled in the art, for example by chromatography. This separation can be carried out either on the products of formula I or on the products of formula II.

The novel antibacterial compositions of the invention are comprised of an antibacterially effective amount of at least one compound of formula I and their non-toxic, pharmaceutically acceptable acid addition salts and an inert pharmaceutical carrier. The compositions may be in the form of tablets, dragees, capsules, granules, suppositories, ointments, creams, gels and injectable solutions or suspensions.

Examples of suitable excipients or inert pharmaceutical carriers are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compositions have a very good antibiotic activity on gram (+) bacteria such as staphylococci, streptococci and particularly on penicillin-resistant staphylococci. Their effectiveness on gram (−) bacteria, notably on coliform bacteria, klebsiella, salmonella, proteus and pseudomonas, is particularly remarkable.

These properties make the compositions useful in the treatment of germ-sensitive illnesses and particularly in that of staphylococcia, such as staphylococcial septicemias, malignant staphylococcia of the face or skin, pyodermatitis, septic or suppurating sores, anthrax, phlegmon, erysipelas, primary or post-influenzal acute staphylococci, broncho-pneumonia, pulmonary suppurations. The composition can also be used as medicaments in the treatment of colibacilloses and associated infections, proteus infections, klebsiella and salmonella and other illnesses caused by gram (−) bacteria.

The novel method of the invention for combatting bacterial infections in warm-blooded animals, including humans, comprises administering to warm-blooded animals an antibacterially effective amount of at least one compound of formula I and their non-toxic, pharmaceutically acceptable acid addition salts. The compounds may be administered rectally, orally, parenterally or topically to the skin or mucous. The usual daily dose is 3.33 to 53.3 mg/kg depending on the condition treated, the compound used and the method of administration.

The novel intermediates of the invention are the compounds of formulae IV and V wherein $R_a$ is an amino protective group.

The compounds of formula II are known and are described in European patent applications No. 0,238,061 and No, 0,266,060. The compounds of formulae III and VI are described in European patent applications No. 153,229, No. 214,029 and No. 282,365.

In the following examples, there are described several preferred embodiments to illustrate the invention. However, it is to be understood that the invention is not intended to be limited to the specific embodiments.

EXAMPLE 1

(+) (cis) (Z) iodide of 2-amino-5-[[7-[[[2-amino-4-thiazolyl][carboxy-(3,4-dihydroxy-phenyl)-methoxy]-imino]-acetamido]-2-carboxy -8-oxo-4-thia-1-aza-bicyclo-[4,2,0]-oct-2-en-3-yl-methyl]thiazolo-[4,5-c]-pyridinium bis(trifluoroacetate)

STEP A: 1,1-dimethylethyl [6S-[6α, 7β(Z)]]-7-[[[[(3,4-dihydroxyphenyl) [(diphenylmethoxy)-carbonyl]-methoxy]-imino] [2-(triphenylmethyl) -amino]-4-thiazolyl]-acetamido]-3-(chloromethyl)-8-oxo-4-thia-1-aza-bicyclo-[4,2,0]-oct-2 -ene-2 -carboxlate A mixture of 600 mg of [[1-(3,4-dihydroxy-phenyl)-2-(diphenylmethoxy)-2-oxo-ethoxy]-imino][2-[(triphenyl-methyl)-amino]-thiazolyl]acetic acid, 115 mg of hydroxy-benzotriazole with 13% water, 240 mg of 1,1-dimethylethyl 3-chloromethyl-7-amino-8-oxo-4-thia-1-aza-bicyclo-[4,2,0]-oct-2-en-2-carboxylate, 6 ml of tetrahydrofuran and 560 microliters of diisopropylcarbodiimide was stirred for 18 hours. The solvent was evaporated off and the residue was chromatographed on silica, (eluant: methylene chloride-methanol (98-2)) to obtain 513 mg of the desired product.

| NMR Spectrum | |
|---|---|
| OtBu | 1.57 (s) |
| CH₂Cl | 4.38 (d) 4.53 (d) 4.68 (d) 4.72 (d) |
| —S—CH₂— | 2.60 to 3.10 (m) |
| —S—CH₂—CH⎪N‖ | 3.88 to 4.10 (m) |
| —C—C—NH—‖O | 8.35 (d) 8.01 (d) |

-continued

| NMR Spectrum | |
|---|---|
| $\overset{H}{\underset{C-NH}{\diagdown\mid\diagup}}$ | 5.46 (d) 5.90 (d) |
| the aromatic protons | 6.58 to 7.40 (m) |

STEP B: 1,1-dimethylethyl [6S-[6α, 7β (Z)]]-7-[[[[(3,4-dihydroxyphenyl) [(diphenylmethoxy)-carbonyl]-methoxy]-imino] [2-(triphenylmethyl)-amino]-4-thiazolyl]-acetamido]-3-(iodomethyl)-8-oxo-4-thia-1-aza-bicyclo-[4,2,0]-oct-2-ene-2-carboxylate 247 mg of the product of Step A, 5 ml of acetonitrile and 54 mg of sodium iodide were stirred for 2 hours at 40° C. After cooling, the sodium chloride formed was filtered and the solvent was evaporated to obtain the desired product which was used as is for the following step.

STEP C: (+) [6S-[6α, 7β (Z)]]-2-amino-5-[[7-[[[[(3,4-dihydroxyphenyl) [(diphenylmethoxy)-carbonyl]-methoxy]imino] [2-(triphenylmethyl)-amino]-4-thiazolyl]-acetamido]-2-[(11-dimethylethoxy)-carbonyl]-8-oxo-4-thia-1-aza-bicyclo-[4,2,0]-oct-2-en-3-yl-]-methyl]thiazolo-[4,5-c]-pyridinium iodide A mixture of the product of Step B, 55 mg of aminothiazolopyridine and 1 ml of dimethyl sulfoxide was stirred for 18 hours at 20° C. The solvent was partly evaporated and the residue was chromatographed on silica (eluant: methylene chloride on its own then methylene chloride-acetone (90-10) and finally methylene chloride-methanol (95-5)) to obtain 124 mg of the desired product.

| NMR Spectrum: DMSO 300 MHz ppm | |
|---|---|
| OtBu | 1.48–149 (s) |
| CH—NH | 5.40 to 5.70 (m) |
| pyridine nucleus protons | 8.95 (s) 9.02 (s) 8.45 to 8.60 (m) |
| —S—$\underline{CH_2}$— | 2.40 to 3.10 (m) |
| —S—CH$_2$—$\underline{CH}$ | 3.95 to 4.05 (m) |
| —C—NH—$\underline{CH}$$\diagup$$\diagdown$ $\overset{\|}{O}$ | 5.40 to 5.70 (m) |
| S—$\underline{CH}$ | 6.59 to 6.82 (m) |

STEP D: (+) (cis) (Z) 2-amino-5- [[7-[[[2-amino-4-thiazolyl][[carboxy-(3,4-dihydroxy-phenyl )-methoxy]-imino]-acetamido]-2- carboxy-8-oxo -4-thia-1-aza-bicyclo-[4,2,0]-oct-2-en3-yl]-methyl]-thiazolo- [4,5,-c]-pyridinium bis (trifluoroacetate) iodide 115 mg of the product of Step C and 0.5 ml of trifluoroacetic acid with 10% anisole were stirred for 2 hours at 20° C. 5 ml of ether were added and the mixture was stirred for 10 minutes. The mixture was separated, washed with ether and dried under reduced pressure to obtain 71 mg of the desired product.

| NMR Spectrum (DMSO 300 MHz) ppm | |
|---|---|
| S—$\underline{CH_2}$— | 2.80 to 2.40 |
| S—CH$_2$—$\underline{CH}$—CH | 3.98 to 4.04 (m) |
| —S—CH$_2$—CH—$\underline{CH}$ | 5.64 (m) |
| —O—$\underline{CH}$—CO$_2$H | 5.23 (s) 5.31 (s) |
| the aromatics | 6.6 to 6.8 |
| —S—$\underline{CH}$ | 6.6 to 6.8 |
| NH | 9.17 |
| $\underline{CH_2}$—N$^\ominus$$\diagup$$\diagdown$ | 5.44 (d) 5.78 (d) |

EXAMPLE 2

(+) (cis) (Z) 7-[[[2-amino-4-thiazolyl] [carboxy-(3,4-dihydroxyphenyl)methoxy]-imino]-acetamido]-8-oxo-3-[3-[(1,3,4-thiadiazol-2-yl)-thio]-1-(E)-propenyl-4-thia-1-aza-bicyclo-[4,2,0]-oct-2,2-carboxylic acid (trifluoroacetate)

STEP A: 1,1-dimethylethyl [6S-[3(E)6α,7β (Z)]]-7-[[[[(3,4-dihydroxy-phenyl) [(diphenylmethoxy)-carbonyl]-methoxy]-imino] [2-(triphenylmethyl)-amino]-4-thiazolyl]-acetamido]-3-[3-[(1,3,4-thiadiazol-2-yl)-thio]-1-propenyl]-8-oxo-4-thia-1-aza-bicyclo-[4,2,0]-oct-2-ene-2-carboxylate 260 mg of 1,1-dimethylethyl 3-[3-[(1,3,4-thiadiazol-2-yl)-thio] -1-propenyl-7-amino-8-oxo-4-thia-1-aza-bicyclo-[4,2,0]-oct-2-ene-2-carboxylate, 480 mg of [[1-(3,4-dihydroxy-phenyl)-2-(diphenylmethoxy) -2-oxo-ethoxy]-imino] [2-[(triphenylmethyl)-amino]-thiazolyl-4-yl] acetic acid, 120 mg of 1-hydroxy benzotriazole hydrate, 5 ml of tetrahydrofuran and 441 ml of 1,3-diisopropylcarbodiimide were stirred for 20 hours at 20° C. The solvent was evaporated and the residue was chromatographed on silica (eluant: methylene chloride-ethyl acetate ( 8-2 )) to obtain 231 mg of the desired product.

| NMR Spectrum CDCl$_3$ MHz ppm | |
|---|---|
| tBu | 1.54 (s) 1.55 (s) |
| H$_6$ and =CH—$\underline{CH_2}$—S | 3.80 to 4.20 |
| H$_7$ cis | 5.34 (dd) 5.89 (dd) |
| O—$\underline{CH}$—C$_6$H$_3$ $\underset{\overset{\|}{O}}{\underset{\|}{\text{—O}}}$ | 2.60–6.24 (dd) 8.35 (m) mobile H's |
| CH=$\underline{CH}$—CH$_2$ (delta E) | 6.47 (m) |
| the aromatics | |
| + =$\underline{CH}$—CH=CH$_2$ | 6.60 to 7.35 |
| + C—$\underline{OCH}$—(C$_6$H$_5$)$_2$ $\overset{\|}{O}$ | |

STEP B: (+) (cis) acid (Z) 7-[[(2-amino-4-thiazolyl] [carboxy-(3,4-dihydroxy-phenyl)-methoxy)-imino]-acetamido]-8-oxo-3-[3-[( 1,3,4-thiadiazol-2-yl)-thio] -1-(E)-propenyl-4-thia-1-aza-bicyclo[4,2,0]-oct-2-ene-2-carboxylate (trifluoroacetate)

A mixture of 215 mg of the product of Step A and 1 ml of trifluoroacetic acid with 10% anisole was stirred at 20° C. for 150 minutes and after 10 ml of ether were added, the mixture was stirred for 10 minutes, followed by separating, washing with ether and drying to obtain 120 mg of the desired product.

| NMR Spectrum DMSO 300 MHz ppm | |
|---|---|
| —S—CH₂—CH | 2.30 to 3.08 |
| NH—CH—CH | 5.57 |
| NH—CH—CH | 4.12 |
| S—CH₂—CH=CH | 4.12 |
| S—CH₂—CH=CH | 6.20 |
| S—CH₂—CH=CH | 6.99 (dd J=15.5 and 10) |
| 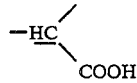 | 5.27 and 5.33 |
| Aromatics | 6.71 to 7.50 |
| NH | 9.28 |
| N=CH<br>\|<br>S | 9.54 |

EXAMPLE 3

(cis) (Z) tetrafluoroborate of 5-[[7-[[[2-amino-4-thiazolyl] [carboxy (3,4-dihydroxy-phenyl)-methoxy]-imino]-acetamido]-2-carboxy-8-oxo-4-thia-1-aza-bicyclo-[4,2,0]-oct-2-en-3-yl]-methyl]-thieno[-2,3-b]-pyridinium (trifluoroacetate)

STEP A: [6S-[6α,7β (Z)]]-4-[[7-[[[[(3,4-dihydroxy-phenyl) [(diphenylmethoxy)-carbonyl]-methoxy]-imino][2-(triphenylmethyl)-amino]-4-thiazolyl]-acetamido]-2-[(1,1-dimethylethoxy)-carbonyl]-8-oxo-4-thia-1-aza-bicyclo-[4,2,0]-oct-2-en-3-yl]-methyl]-thieno-[2,3-b]-pyridinium tetrafluoroborate 200 mg of the product of Step A of Example 1 were added to a mixture of 57 mg of silver tetrafluoroborate, 53 mg of thieno[2,3-b]-pyridine and 20 ml of methylene chloride. The mixture was stirred for one hour and then another 57 mg of silver tetrafluoroborate and 53 mg of thieno-[2,3-b]-pyridine were added. After stirring for one hour, the solvent was evaporated. The residue was chromatographed on silica (eluant: methylene chloride-methanol 85/15) to obtain 123 mg of the desired product.

STEP B: (cis) (Z) tetrafluoroborate of 5-[7-[[[2-amino-4-thiazolyl] [carboxy-(3,4-dihydroxy-phenyl)-methoxy]-imino]-acetamido]-2-carboxy-8-oxo-4-thia-1-aza-bicyclo-[4,2,0-oct-2-en-3-yl]-methyl]-thieno-[2,3-b]-pyridinium (trifluoroacetate)

123 mg of the product of Step A were stirred for 2 hours with 1 ml of trifluoroacetic acid with 10% anisole. 10 ml of a 1—1 mixture of ethyl ether and isopropylether were added and the mixture was stirred for 30 minutes, followed by separating, washing and drying to obtain 81 mg of the desired product.

| NMR Spectrum DMSO 300 MHz ppm | |
|---|---|
| —S—CH₂ | 2.8 to 3.4 (m) |
| —S—CH₂—CH | 3.89 (m) |
| 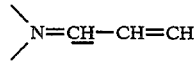 | 5.59 (dd) |
| O—N= | 5.25 (s) (70% S) |
| | 5.32 (s) (30% R) |
| 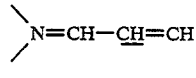 | |
| the phenyl H's | 6.6 to 6.8 (m) |
| —S—CH=CH— | 7.91 (d, j=6Hz) |
| —S—CH=CH | 8.29 (d) |
| 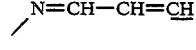 | 9.24 (m) |
| \<br>N=CH—CH=CH<br>/ | 8.19 (m) |
| \<br>N=CH—CH=CH<br>/ | 9.14 (m) |
| mobile H's | 7.28 (m) 9.00 (m) |

PREPARATION OF EXAMPLE 4

1,1-dimethylethyl [6S-[3)-(E)-6α, 7β (Z)]]-7-[[[[[3,4-bis[(2-methoxyethoxy)-methyl]-phenyl] [(diphenyl-methoxy)-carbonyl]-methoxy]-imino] [2-(triphenylmethyl)-amino]-4-thiazolyl]-acetamido] -3-[3-iodo-1-propenyl]-8-oxo-4-thia-1-aza-bicyclo-[4,2,0]-oct-2-ene-2-carboxylate STEP A: 1,1-dimethylethyl [6S-3 (E) 6α,7β (Z)]]-7-[[[[[3,4-bis[(2-methoxyethoxy)-methoxy]-phenyl] [(diphenyl-methoxy)-carbonyl]-methoxy]-imino] [2-(triphenylmethyl)-amino]-4-thiazolyl-acetamido]-3-[3-hydroxy-1-propenyl]-8-oxo-4-thia-1-aza-bicyclo-[4,2,0]-oct-2-ene-2-carboxylate A solution of 0.324 ml of N,N-diisopropylcarbodiimide in 1 ml of methylene chloride was added at −10° C. to a solution of 1 g of [[1-(3,4-bis[(2-methoxyethoxy)- methoxy]-phenyl]-2-(diphenyl-methoxy) -2-oxo-ethoxy]-imino] [2-[(triphenyl-methyl)-amino]-thiazolyl-4-yl] acetic acid and 366 mg of 1,1-dimethylethyl 3-hydroxy-1-propenyl-7-amino-8-oxo-4-thia-1-aza-bicyclo-[4,2,0]-oct-2-ene-2-carboxylate in 10 ml of methylene chloride. The mixture was stirred at −20° C. for 30 minutes and the reaction medium was chromatographed on silica (eluant: ethyl acetate) to obtain 0.756 g of the desired product.

| IR Spectrum (CHCl3) | |
|---|---|
| OH | at 3610 cm$^{-1}$ |
| =C—NH | 3440–3402 cm$^{-1}$ |
| \C=O/ | 1777–1730–1700–1662 cm$^{-1}$ |
| Aromatic + C=C + Amide II | 1596-1565-1526-1497 cm$^{-1}$ |

STEP B: 1,1-dimethylethyl [6S-[3(E)6α, 7β (Z)]]-7-[[[[[3,4-bis [(2-methoxyethoxy)-methoxy]-phenyl][-(diphenyl-methoxy)-carbonyl]-methoxy]-imino] [2-(triphenylmethyl)-amino]-4-thiazolyl]-acetamido]-3-[3-iodo-1-propenyl]-8-oxo-4-thia-1-aza-bicyclo-[4,2,0-oct-2-ene-2-carboxylate 0.047 ml of 2,6-lutidine was added to a mixture of 0.250 g of the product of Step A, 5 ml of methylene chloride and 49 mg of tetrabutyl ammonium iodide and then the solution was cooled down to −70° C. A solution of 1.44 ml of trifluoromethane sulfonic anhydride in 0.5 ml of methylene chloride was added, followed by stirring for 5 minutes at −70° C. 10 ml of a 0.2N aqueous solution of sodium thiosulfate were then added, and after stirring for 5 minutes, extraction was done with methylene chloride. The extracts were washed, dried and the solvent was evaporated. The residue was chromatographed on silica (eluant: methylene chloride-ethyl acetate (8-2)) to obtain 177 mg of the desired product.

| NMR Spectrum CDCl3 (300 MHz) ppm | |
|---|---|
| CO2tBu | 1.54 (s) 1.56 (s) |
| CH2 in position 1 | 2.30 to 2.90 (m) |
| 2 OCH3 | 3.24 (s) 3.33 (s) 3.37 (s) 3.38 (s) |
| the 2 O—CH2—CH2—O's | 3.42 (m) to 3.60 (m) 4H |
| | 3.70 (m) to 3.90 (m) 4H |
| H6 | 3.97 (m) |
| CH—C<u>H</u>2—X | 4.06 (dd) |
| the 2-C6H5—C<u>H</u>2—O's | 5.25 to 5.35 (m) |
| H7 | 5.61 (m) |
| C6H5—C<u>H</u>—O | 5.96 (s) 6.06 (s) |
| =C<u>H</u>—CH2-(delta E) | 6.35 (resolved dt) |
| approx. 33 to 34 H aromatic H, CO2—C<u>H</u>—(C6H5)2 | 6.58 to 7.35 (m) |
| the other CH=H5 thiazoles | |

| NMR Spectrum CDCl3 (300 MHz) ppm | |
|---|---|
| CO—N<u>H</u>—CH | 7.87 (d) 8.07 (d) |

EXAMPLE 4

(+) (cis) (Z) internal salt of 5-[3[7-[[(2-amino-4-thiazolyl) [carboxy-(3,4-dihydroxy-phenyl)-methoxy]-imino]-acetamido]-2-carboxy-8-oxo-4-thia-1-aza-bicyclo-[4,2,0]-oct-2-en-3-yl]-thiazolo-[4,5-c]-pyridinium STEP A: [6S-[3(E)6α, 7β (Z)]]-5-[3-[7-[[[[[3,4-bis[(2-methoxyethoxy)-methoxy]-phenyl]-[(diphenyl-methoxy)-carbonyl]-methoxy]-imino]-[2-(triphenylmethyl)-amino-4-thiazolyl]-acetamido]-2-[(1,1-dimethylethoxy)-carbonyl]-8-oxo-4-thia-1-aza-bicyclo-[4,2,0]-oct-2-en-3-yl]-2 -propenyl]-thiazolo-4,5-c]-pyridinium A mixture of 107 mg of 1,1-dimethylethyl [6S-[3(E) -6α, 7β (Z)]]-7-[[[[[3,4-bis[(2-methoxyethoxy)-methoxy]-phenyl]-[(diphenylmethoxy)-carbonyl]-methoxy]-imino] [2- (triphenylmethyl)-amino]-4-thiazolyl]-acetamido]-3-[3-iodo-1-propenyl]-8-oxo-4-thia -1-aza-bicyclo-[4,2,0]-oct-2-ene-2-carboxylate, the product of Step B of the preparation of Example 4 and 11.4 mg of thiazolo-[4,5-c]pyridine with 0.4 ml of dimethyl sulfoxide was stirred for 24 hours. After evaporation to dryness, the residue was chromatographed on silica (eluant: methylene chloride-methanol (92-8)) to obtain 82 mg of the desired product which was used as is for the following step. STEP B: (+) (cis) (Z) internal salt of 5-[3-[7-[[(2-amino-4-thiazolyl) [carboxy-(3,4-dihydroxy-phenyl)-methoxy]-imino]-acet-amido]-2-carboxy-8-oxo-4-thia-1-aza-bicyclo-[4,2,0]-oct-2-en-3-yl]-2-propenyl]-thiazolo-[4,5-c]-pyridinium A solution cooled to 0° C. of 4.3 ml of trifluoroacetic acid in 2.2 ml of methylene chloride was added at 0° C. to a solution of 107 mg of the product of Step A, 2.2 ml of methylene chloride and 0.45 ml of anisole. The mixture was stirred for one hour at 0° C. and concentrated under reduced pressure. The residue was taken up in ether and separated to obtain 45 mg of product which was stirred for one hour at 0° C. with 1.6 ml of a trifluoroacetic acid solution with 10% anisole and treated as above to obtain 37.2 mg of the expected product.

| NMR Spectrum DMSO 400 MHz | |
|---|---|
| S—C<u>H</u>2—CH | 2.71–2.89–3.06–3.21 (m) |
| H6 | 3.91–3.98 (m) |
| N—O—C<u>H</u>—C6H5 | 5.26–5.32 (s) |
| ⊖N—CH2—C | 5.53 (m) |
| H7 | 5.57 (m) |
| CH= | 6.38 (m) delta E |
| Aromatic + Thiazole Other ethylenics | 6.7 to 7.35 (m) |
| H6' and H7' | approx. 8.93 approx. 8.85 (dd) |
| H4' and H2' | 9.93–10.05 (s, d) |
| Mobile proton | 7.30–9.10; 9.28 and 12.95 |

EXAMPLE 5

(+) (cis) (Z) internal salt of 4-[3-[7-[[(2-amino-4-thiazolyl)-[carboxy-(3,4-dihydroxy-phenyl)-methoxy]-imino]-acetamido]-2-carboxy-8-oxo-4-thia-1-aza-bicyclo-[4,2,0]-oct-2-en-3-yl]-2-propenyl]-thieno-[3,2-b]-pyridinium STEP A: [6S-[3 (E)-6α, 7β (Z) ]]-4-[3-7-[[[[[3,4-bis-[(2-methoxyethoxy)-methoxy]-phenyl] [(diphenylmethoxy)-carbonyl]-methoxy]-imino] [2-(triphenylmethyl)-amino]-4-thiazolyl]-acetamido]-2[(1,1-dimethylethoxy) -carbonyl]-8-oxo-4-thia-1-aza-bicyclo-[4,2,0]-oct-2-en-3-yl]-2-propenyl]-thieno-[3,2-b]-pyridinium trifluoromethansulfonate 0.079 ml of trifluoromethane sulfonic anhydride was added at −60° C. to a solution of 240 mg of the product of Step A of the preparation of Example 4 and 104.8 mg of thieno-[3,2-b]-pyridine with 8 ml of methylene chloride. The mixture was stirred for 5 minutes at -60° C. and then left to return to 0° C. over 30 minutes. 1 ml of water was added, followed by decanting, and after drying, the residue was evaporated to dryness under reduced pressure. The 423 mg of residue was chromatographed on silica (eluant: methylene chloride-methanol (95-5)) to obtain 210 mg of the desired product which was used as is for the following step.

STEP B: (+) (cis) (Z) internal salt of 4-[3-[7-[[2-amino-4-thiazolyl) [carboxy-(3,4-dihydroxy-phenyl)-methoxy]-imino]-acet-amido]-2-carboxy-8-oxo-4-thia-1-aza-bicyclo-[4,2,0]-oct-2-en-3-yl]-2 -propenyl]-thieno-[3,2-b]-pyridinium A solution of 10 ml of trifluoroacetic acid in 5 ml of methylene chloride cooled to 0° C. was added at 0° C. to a solution of 210 mg of the product of Step A, 5 ml of methylene chloride and 1 ml of anisole. The mixture was stirred for one hour at 0° C. and the solvents were evaporated. The residue was taken up in 10 ml of ether. After separating, washing and drying, 68 mg of the expected product were obtained.

| NMR Spectrum DMSO 250 MHz | |
| --- | --- |
| H6 | 3.96 (m) |
| C6H5—CH—O | 5.25–5.32 |
| H7 | 5.56 (resolved d after exchange) |
| ⊕N—CH2 | 5.74 (wide line) |
| 1H ethylenic delta E | 6.33 (resolved d) |
| H6' and H3' or H2' | 8.05 to 8.15 (m) (2H) |
| H3' or H2' | 8.86 (d) |
| H5' or H7' | 9.18 (d, 1) and 9.37 (d) |
| Mobile protons | 7.31 |
| Aromatics, H5 of the thiazole and the other ethylenic | 6.7 to 7.4 (m) |
| S—CH2 (partly masked by the dimethyl sulfoxide) | approx. 2.4 to 2.5 |

EXAMPLE 6

(+) (cis) (Z) internal salt of 7-[3-[7-[[(2-amino-4-thiazolyl) [carboxy-(3,4-dihydroxy-phenyl)-methoxy]-imino]-acetamido]-2-carboxy-8-oxo-4-thia-1-aza-bicyclo-[4,2,0]-oct-2-en-3-yl]-2-propenyl]-thieno-[3,2-b]-pyridinium STEP A: [6S[3(E)-6α, 7β (Z)]]-7-[3-7-[[[[[3,4-bis](2-methoxy ethoxy)-methoxy]-phenyl] [(diphenyl methoxy)-carbonyl]methoxy]imino][2-(triphenylmethyl)-amino]-4-thiazolyl]-acetamido]-2-[(1,1-dimethylethoxy)-carbony]-8-oxo-4-thia-1-aza-bicyclo-[4,2,0]-oct-2-en-3-yl]-2-propenyl]-thieno-[3,2-b]-pyridinium trifluoromethanesulfonate 0.3 ml of a solution of 1 ml of trifluoromethane sulfonic anhydride in 4 ml of methylene chloride was added at −70° C. to a mixture of 86 mg of thieno-[2,3-b]-pyridine, 6 ml of methylene chloride and 200 mg of the product of Step A of the preparation of Example 4. The mixture was stirred for 10 minutes at −70° C. and then the temperature was allowed to return to 20° C. over one hour. 2 ml of water were added, followed by decanting, drying and concentrating under reduced pressure. The residue was chromatographed on silica (eluant: methylene chloride-methanol (92-8)) to obtain 123 mg of the desired product which was used as is for the following step.

STEP B: (+) (cis) (Z) internal salt of 7-[3-[7-[[(2-amino-4-thiazolyl) [carboxy-(3,4-dihydroxy-phenyl)-methoxy]-imino]-acetamido]-2-carboxy-8-oxo-4-thia-1-aza-bicyclo-[4,2,0]-oct-2-en-3-yl]-2-propenyl]-thieno-[3,2-b]-pyridinium 6.95 ml of trifluoroacetic acid in solution in 3.5 ml of methylene chloride were added at 0° C. to a solution of 139 mg of the product of Step A in 3.5 ml of methylene chloride and 0.69 ml of anisole. The mixture was stirred for 75 minutes at 0° C. and concentrated to dryness under reduced pressure. The dry extract was taken up in ether, separated, washed and dried to obtain 70 mg of product which was taken up again in 1.75 ml of methylene chloride and 0.34 ml of anisole. 3.48 ml of trifluoroacetic acid in 1.75 ml of methylene chloride were added at 20° C., and the mixture was stirred for 10 minutes at 20° C. Then, the solution was evaporated to dryness under reduced pressure and the dry extract was taken up in ether, then separated, washed and dried to obtain 43 mg of the desired product.

| NMR Spectrum DMSO 300 MHz ppm: | |
| --- | --- |
| CH2S | 2.70 to 3.10 |
| H6 | 3.93 |
| OCH2O of the MEM's | 5.0 to 5.10 |
| C6H5—CHO / CO | 5.25 (s) 5.32 (s) |
| H7 (cis/H6) | 5.58 (d after exchange) |
| =C—CH2N⊕ | 5.59 (d after exchange) 5.70 |
| H5 thiazole | 6.69 or 6.80 (s) |
| CH=CH + Aromatic + NH2 | 6.68 to 7.31 |

-continued

| NMR Spectrum DMSO 300 MHz ppm: | |
| --- | --- |
| CH=CH—CH$_2$ | 6.19 (dt) |
| H$_2'$ and H$_3'$ | 7.89 (d) and 8.28 (d) |
| H$_5'$ | 8.15 (t) |
| H$_4'$ | 9.09 (d) |
| H$_6'$ | 9.20 (d) |
| The C—NH—CH's<br>‖<br>O | 9.29 (m) |

EXAMPLE 7

(+) (cis) (Z) internal salt of 7-[3-[7-[[(2-amino-4-thiazolyl) [carboxy-(3,4-dihydroxy-phenyl)-methoxy]-imino]acetamido]-2-carboxy -8-oxo-4-thia-1-aza-bicyclo-[4,2,0]-oct-2-en-3-yl]-2-propenyl]-thieno-[2,3-b]-pyridinium 6.15 ml of trifluoroacetic acid were added at 0° C. to a solution of 123 mg of the product of Step A of Example 6 in 2.8 ml of methylene chloride and 0.6 ml of anisole. The mixture was stirred for 15 minutes at 0° C., then for 5 hours at 20° C. After concentration to dryness under reduced pressure, the residue was taken up in ether, separated, washed and dried to obtain 57 mg of product which was dissolved in a 50—50 mixture of acetonitrile and water with 50 microliters of triethylamine. The solution was chromatographed on a Bondapack Cls support (eluant: acetonitrile - water (50—50)), evaporated to a small volume under reduced pressure, then lyophilized to obtain 45 mg of the desired product to which 15 mg derived from a first operation were added. A new chromatography was carried out on an RP18 support eluting with acetonitrile - water (50—50). Concentration was carried out to a reduced volume under reduced pressure and a small amount of water was added, followed by lyophilization to obtain 33 mg of the desired product.

| NMR Spectrum DMSO 300 MHz ppm: | |
| --- | --- |
| CH$_2$S | 3.75 (m) |
| H$_6$ | 3.96 (m) |
| C$_6$H$_5$—CH—CO | 5.23 (s)–5.36 (s) |
| H$_7$ | 5.42 (dd, d after exchange) |
| =CH—CH$_2$—N$^\oplus$ | 5.57 (m) |
| =CH—CH$_2$ | 5.90 (m) |
| aromatic H<br>thiazole H$_5$<br>ethylenic H | 6.60 to 7.40 (m) |
| H$_5'$ | 8.12 (m) |
| H$_2'$ and H$_3'$ | 7.87 (d) 8.26 (d) |
| H$_4'$ | 9.05 |
| H$_6'$ | 9.20 |

EXAMPLE 8

(+) (cis) (Z) internal salt of 2-amino 5-[3-[7-[[(2-amino-4-thiazolyl) [[carboxy-(3,4-dihydroxy-phenyl)-methoxy]-imino]-acetamido]-2-carboxy-8-oxo-4-thia-1-aza-bicyclo-[4,2,0]-oct-2-en-3-yl]-2-propenyl]-thiazolo-4,5-c]-pyridinium STEP A: [6S[3(E) 6α, 7β (Z) ]]-2-amino-5-[3-[7-[[[[[3,4-bis[(2-methoxyethoxy)-methoxy]-phenyl] [(diphenyl-methoxy)-carbonyl]-methoxy]-imino] [2-(triphenylmethyl-amino)-4-thiazolyl]-acet-amido]-2- [(1,1-dimethylethoxy)-carbonyl]-8-oxo-4-thia-1-aza-bicyclo-[4,2,0] -oct-2-en-3-yl]-2-propenyl]-thiazolo-[4,5-c]-pyridinium A mixture of 200 mg of the product of Step B of the preparation of Example 4, 36.2 mg of aminothiazolopyridine and 3 ml of dimethylsulfoxide was stirred for 7 hours. After evaporation of the solvent under reduced pressure, the residue was chromatographed on silica (eluant: methylene chloride-methanol (9-1)) to obtain 156 mg of the desired product.

STEP B: (+) (cis) (Z) internal salt of 2-amino-5-[3-[7-[[(2-amino -4-thiazolyl)[carboxy-(3,4-dihydroxyphenyl)-methoxy-]-imino]-acetamido]-2-carboxy-8-oxo-4-thia-1-aza-bicyclo-[4,2,0-]oct-2-en-3-yl]-2-propenyl]-thiazolo-[4,5-c]-pyridinium A solution cooled to 0° C. of 4 ml of methylene chloride and 7.4 ml of trifluoroacetic acid was added at 0° C. to a solution of 155.6 mg of the product of Step A in 4 ml of methylene chloride and 0.75 ml of anisole. The mixture was stirred for one hour at 0° C. and evaporated to dryness under reduced pressure. The residue was crystallized from ether to obtain 57 mg of product which was treated at 0° C. for one hour with 2 ml of a trifluoroacetic acid solution with 10% anisole. The treatment was carried out as above and the operation was repeated once again to obtain 31.5 mg of the desired product.

| NMR Spectrum DMSO 400 MHz ppm | |
| --- | --- |
| resolved H$_7$ | 5.54 (dd) 5.59 (dd) |
| 1-CH delta E | 6.33 (m) |
| C$_6$H$_5$—CO—O | 5.26 (s)–5.33 (s) |
| N$^\oplus$—CH$_2$ | 5.30 (m) |
| Aromatic +<br>thiazole H$_5$ +<br>ethylenic H | 6.7 to 7.3 (m) |
| S—CH$_2$—CH | 2.3 (m) 2.69 (m) 2.89 (m) 3.06 (m) |
| H$_6'$ and H$_7'$ | 8.43 (m) 8.49 (m) |
| H$_4'$ | 9.02 (d) |
| NH—CH | 9.26 and 9.30 (d) |
| mobile protons | 12.9 and 13.5 |

EXAMPLE 9

Injectable preparations were prepared containing 500 mg of the product of Example 3 and sterile aqueous excipient sufficient for a volume of 5 ml.

PHARMACOLOGICAL STUDY

In vitro activity, method of dilutions in a liquid medium.

A series of tubes were prepared into which the same quantity of sterile nutritive medium was distributed. Increasing quantities of the product to be studied were distributed into each tube and then each tube was sown with a bacterial strain. After incubation for twenty-four hours in an oven at 37° C., the growth inhibition evaluated by trans-illumination, which allowed the minimal inhibiting concentrations to be determined (M.I.C. express in g/$^{ml}$). The following results were obtained:

| STRAINS | Product of Example 1 | Product of Example 3 |
|---|---|---|
| Pseudomonas aeruginosa 1771 | 1.25 | 0.6 |
| Pseudomonas aeruginosa 1771 m | 0.6 | 0.15 |
| Pseudomonas aeruginosa ATCC 9027 | 1.25 | 0.6 |

Various modifications of the products and method of the invention may be made without departing from the spirit or scope thereof and it is to be understood that the invention is intended to be limited only as defined in the appended claims.

What is claimed is:

1. The syn isomer a quaternary ammonium compound of the formula

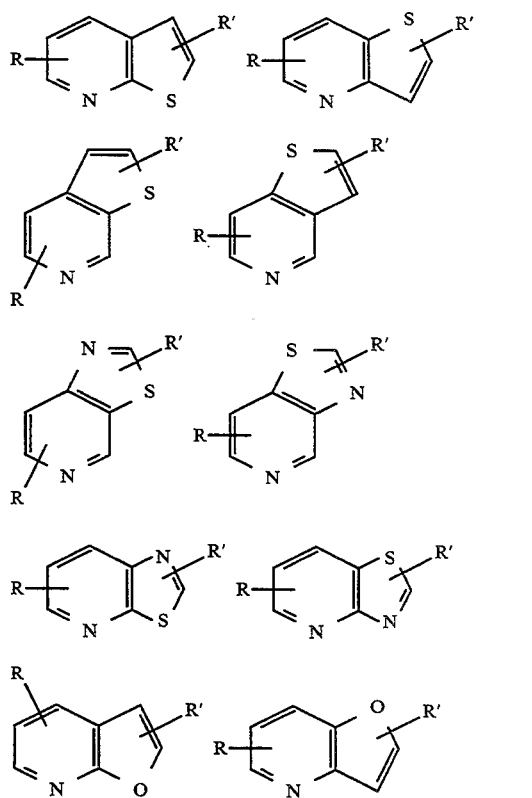

in the R or S form or a mixture of R and S forms wherein $R_1$ is selected from the group consisting of

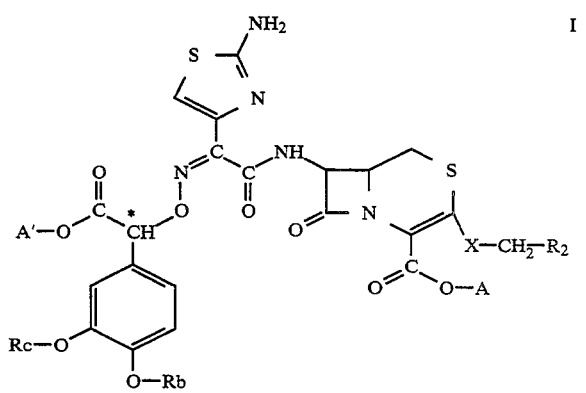

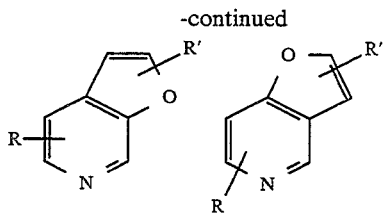

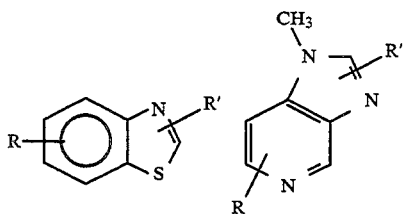

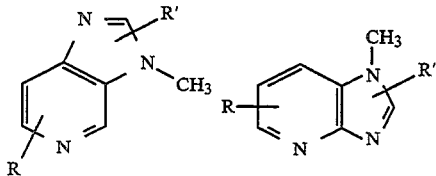

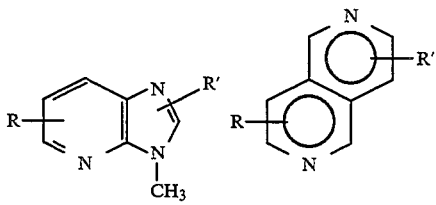

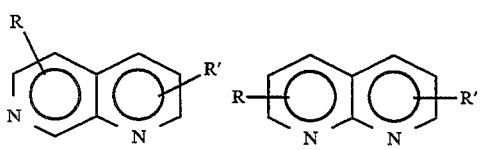

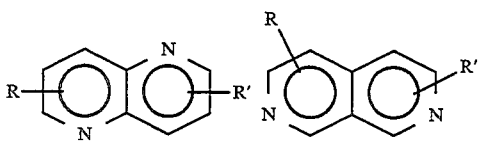

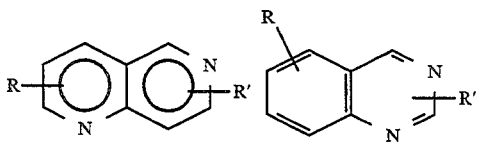

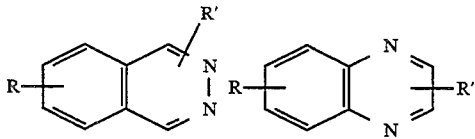

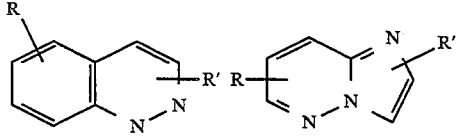

-continued

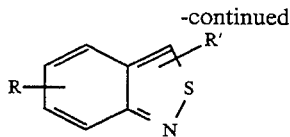

R and R' are individually selected from the group consisting of hydrogen, alkyl of 1 to 4 carbon atoms, alkoxy of 1 to 4 carbon atoms, halogen,

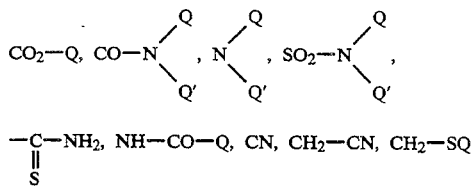

—NH₂, NH—CO—Q, CN, CH₂—CN, CH₂—SQ

Q and Q' are individually selected from the group consisting of hydrogen and alkyl of 1 to 4 carbon atoms, X is a single bond or $$\begin{matrix}\diagdown\\ \diagup\end{matrix}C=C\begin{matrix}\diagup\\ \diagdown\end{matrix}$$

in E or Z form, $R_b$ and $R_c$ are individually selected from the group consisting of an equivalent of alkali metal or alkaline earth metal, magnesium, ammonium and amino or A and A' are the remainder of an easily cleavable ester group or —CO₂A is —CO₂$^\theta$ and their nontoxic, pharmaceutically acceptable acid addition salts.

2. A compound of claim 1 wherein $R_1$ is selected from the group consisting of

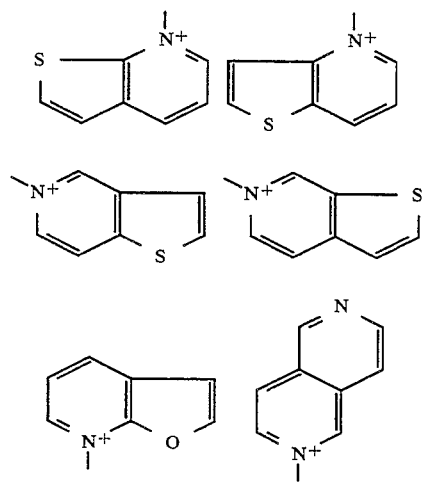

3. A compound of claim 1 wherein $R_1$ is selected from the group consisting of

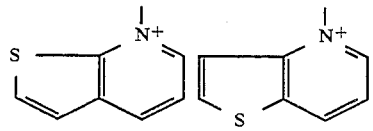

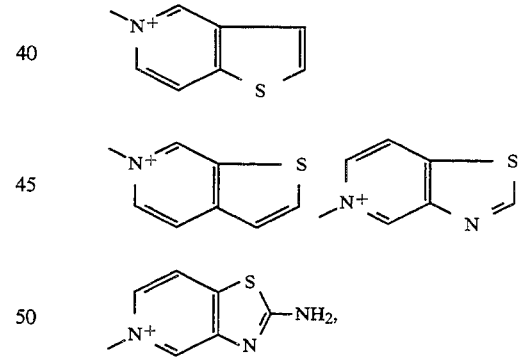

1,3,4-thiadiazolylthio and methyltetrazolyl.

4. A compound of claim 1 wherein $R_1$ is

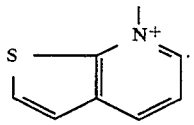

5. A compound of claim 1 selected from the group consisting of (S) (cis) (Z) 5-[[7-[[(2-amino-4-thiazolyl) [carboxy-(3,4-dihydroxy-phenyl) -methoxy]-imino]-acetamido]-2-carboxy-8-oxo -4-thia-1-aza-bicyclo-[4,2,0]-oct-2-en-3-yl]-methyl]-thieno-[2,3-b]-pyridinium in R or S form or in the form of an R,S mixture and in the form of an internal salt or a salt with alkali metals, alkaline-earth metals, magnesium, ammonium hydroxide, amino organic bases, acids and its easy cleavable esters.

6. An antibacterial composition comprising an antibacterially effective amount of at least one compound of claim 1 and an inert pharmaceutical carrier.

7. A composition of claim 6 wherein $R_1$ is selected from the group consisting of

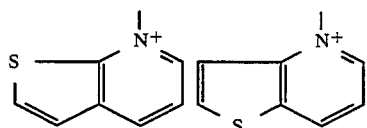

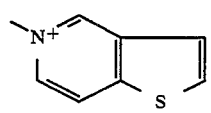

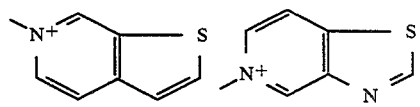

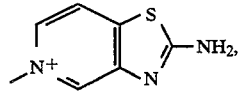

1,3,4-thiadiazolylthio and methyltetrazolyl.

8. A composition of claim 7 wherein $R_1$ is

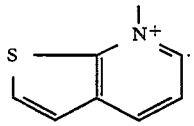

9. A method of treating bacterial infections in warm-blooded animals comprising administering to warm-blooded animals a bactericidally effective amount of a compound of claim 1.

10. The method of claim 9 wherein $R_1$ is selected from the group consisting of

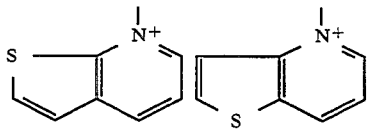

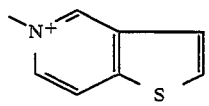

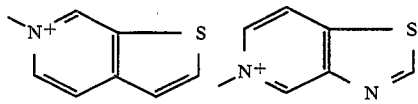

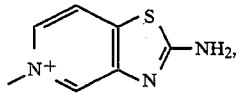

1,3,4-thiadiazolylthio and methyltetrazolyl.

11. The method of claim 9 wherein $R_1$ is

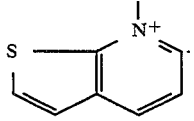

* * * * *